United States Patent [19]

Ishida

[11] Patent Number: 5,152,939
[45] Date of Patent: Oct. 6, 1992

[54] COMPOSITE DENSIFICATION WITH BENZOXAZINES

[75] Inventor: Hatsuo Ishida, Shaker Heights, Ohio

[73] Assignee: Edison Polymer Innovation Corp., Brecksville, Ohio

[21] Appl. No.: 668,014

[22] Filed: Mar. 12, 1991

[51] Int. Cl.$^5$ .................. B29C 71/02; B32B 9/00
[52] U.S. Cl. ........................ 264/29.1; 264/29.7; 264/347; 264/29.6; 525/129; 528/153
[58] Field of Search ............ 264/29.5, 29.7, 60, 264/63, 66, 29.1, 347, 29.6; 423/447.1, 448; 528/153; 525/129

[56] References Cited

U.S. PATENT DOCUMENTS

| | | |
|---|---|---|
| Re. 32,745 | 9/1988 | Schreiber . |
| 4,501,864 | 2/1985 | Higginbottom . |
| 4,507,428 | 3/1985 | Higginbottom et al. . |
| 4,557,979 | 12/1985 | Higginbottom et al. . |
| 4,659,624 | 4/1987 | Yeager et al. .......... 264/29.1 |
| 4,714,752 | 12/1987 | Sokalski . |
| 4,719,253 | 1/1988 | Turpin et al. . |
| 4,806,267 | 2/1989 | Culbertson et al. . |

OTHER PUBLICATIONS

Chemical Abstracts, vol. 83, 1975:83:117206b.
Chemical Abstracts, vol. 85, 1976:85:22857s.
Chemical Abstracts vol. 19, 1979:91:41002z; 91:58829x; 91:58830r.
Chemical Abstracts, vol. 93, 1980:93:96970k.
Chemical Abstracts, vol. 94, 1981:94:5022j.
Chemical Abstracts, vol. 95, 1981:95:44856z.
Chemical Abstracts, vol. 97, 1982:97:40429f.

*Primary Examiner*—Jeffery Thurlow
*Assistant Examiner*—Mathieu Vargot
*Attorney, Agent, or Firm*—D. Peter Hochberg; Mark Kusner; Louis J. Weisz

[57] ABSTRACT

A method for forming carbon-carbon composites consists of impregnating structures with carbon-forming precursor compounds comprising multi-functional benzoxazine compounds. The impregnated structures are pyrolyzed to form carbonaceous char which serves to fill the interstices in the structure, thus densifying the composites. The process of impregnation and pyrolysis is repeated as many times as required to obtain the composite density desired. Unusually high char yields are produced by multi-functional benzoxazine compounds in which benzoxazine are joined to each other through a bridge characterized by having conjugated unsaturation associated therewith. A number of preferred compounds providing unexpectedly high yields of char are shown, enabling the desired densification to be achieved with a minimum number of impregnation and pyrolysis cycles, thereby reducing the costs of forming the composites.

10 Claims, No Drawings

COMPOSITE DENSIFICATION WITH BENZOXAZINES

This process relates to the preparation of carbon-carbon composite materials. More particularly, this invention relates to the use of materials providing improved carbon yields useful for densifying fibrous structures of carbon during formation of carbon-carbon composites. Specifically, this invention relates to the use of particular multi-functional benzoxazine compounds to densify structural networks formed by carbon fibers in the process of fabricating carbon fiber reinforced carbonaceous composites.

BACKGROUND OF THE INVENTION

Carbon-carbon composites, that is, carbonized material reinforced with carbon fibers consisting essentially of elemental carbon and some graphitic materials can be prepared in a wide variety of shapes exhibiting a number of unique properties. Importantly, such materials possess unusual resistance to high temperature environments, for example, they show thermal stability as a solid, and due to their high thermal conductivity and low thermal expansion behavior, they resist thermal shock. The materials also maintain a high degree of strength and stiffness when exposed to high temperatures. Such properties are explained by the high refractive nature of elemental carbon and by the high strength and stiffness of fibers formed from amorphous and graphitic carbon.

In view of the preceding, therefore, it is not surprising that carbon-carbon composites have found, and will continue in the future to find broad use in lightweight, aerospace applications. They are, for example, widely used in the field of space vehicle re-entry, and in this regard, the space shuttle employs carbon-carbon composites in its nose cone and wing edges. Disc brakes for high performance aircraft provide another application depending upon the unique properties of carbon-carbon composites.

While carbon-carbon composites possess many valuable characteristics, including those mentioned, they suffer from the disadvantage of being expensive to fabricate; thus their use is normally restricted to applications in which properties, rather than cost are of primary importance. The high cost of the composites is due to an important degree to their method of fabrication, which necessarily involves multi-step processing, as will be explained in the following.

In a typical procedure, the composites are formed by arranging carbon fibers in a two, three or four directional, occasionally unidirectional reinforcing structure, which is impregnated with a carbon-containing compound that functions as a precursor for the carbon matrix. Following impregnation, the structure is heated in a carbonization step conducted under an inert atmosphere to the decomposition temperature of the precursor, for example in an autoclave, thereby producing a more dense fibrous structure whose interstices are at least partially filled with carbon resulting from the pyrolysis of the precursor material. The structure thus processed is then removed from the autoclave, reimpregnated with additional matrix precursor and again subjected to a carbonization treatment, resulting in additional filling of the composite's interstices with carbon. The procedure is repeated, frequently as many as four to twenty times, until satisfactory composite densification has occurred.

Unfortunately, each carbonization cycle required to achieve the desired densification is both time consuming and labor intensive and, therefore, costly. Consequently, it will be appreciated that the precursors should have a high carbon or "char" yield, i.e., a low weight loss during the carbonization treatments. The use of precursors yielding a high char level assures the greatest possible yield of carbon from each carbonization cycle, thus minimizing the number of cycles required and the cost necessarily entailed in the process.

In addition to an ability to form relatively high amounts of carbon char, it is advantageous for composite matrix precursors to exhibit a low viscosity as well as the ability to wet the surfaces of the carbon substrates being impregnated. In this regard, viscous materials are undesirable since it is difficult to accomplish satisfactory penetration of such substances into the interstices of the carbon structure, particularly since the interstices grow smaller with each successive carbonization cycle. Furthermore, while precursors that flow readily during the impregnation portion of the cycle are of advantage since they facilitate penetration throughout the interior of the structure, the precursors should desirably resist flow during the carbonization process. This apparent anomaly is explained by the fact that liquid flow must be inhibited during the process of heating the precursor materials within the filamentary carbon structure to their decomposition temperature in order to avoid loss of the materials from the structure.

In an effort to provide superior matrix formation, various materials have been used in the past to form carbon-carbon composites. Coal tar pitch is among such materials, and while it is capable of yielding relatively high levels of char; it is a relatively viscous material, making the impregnation process difficult. In addition, high carbon yields from coal tar pitch are possible only if the carbonization process is performed very slowly or under relatively high pressure, for instance, in the neighborhood of 100 bars. Also, the viscosity of such pitches decreases with temperature, producing undesirable liquid loss during heat-up of the composite structure to the pyrolysis temperature of the pitches.

Precursors comprising thermosetting resins, on the other hand, do not need to be subjected to pressure during carbonization, and since they undergo cure prior to carbonization, they are not characterized by the disadvantage of tending to separate from the composite structure before precursor carbonization. Unfortunately, however, the char yield of thermosetting resins, which can in some cases be in the order of 39-51%, is not particularly high, necessitating relatively more carbonization cycles. Various other precursors have also been suggested and used in the past with varying results, but the search for precursors displaying optimal results in the formation of carbon-carbon composites has proceeded.

BRIEF DESCRIPTION OF THE INVENTION

In view of the foregoing, therefore, it is a first aspect of this invention to provide carbon precursor compounds useful in fabricating carbon-carbon composites.

A second aspect of this invention is to provide a method for fabricating carbon-carbon composites utilizing fewer carbonization cycles.

An additional aspect of this invention is to provide carbon-forming precursor compounds for carbon-carbon composites that permit improved densification of the composites to be achieved.

A further aspect of this invention is to provide carbon precursor compounds for carbon-carbon composites that produce a high carbon yield upon pyrolysis.

An additional aspect of this invention is to provide carbon-forming precursor compounds for carbon-carbon composites that can be cured to prevent their inadvertent loss from skeletal carbon structures prior to their pyrolysis.

Another aspect of this invention is to provide carbon precursor compounds that display relatively low viscosities during impregnation and prior to being cured.

Yet another aspect of this invention is to provide carbon precursor compounds for carbon-carbon composites that exhibit superior shelf life.

The foregoing and additional aspects of this invention are provided by a process for forming a carbon-carbon composite comprising impregnating carbon fibers with a multi-functional benzoxazine compound and pyrolyzing said compound to form a carbon-carbon composite.

The preceding and other aspects of this invention are provided by a process for forming a carbon-carbon composite comprising impregnating carbon fibers with a benzoxazine compound selected from the group consisting of

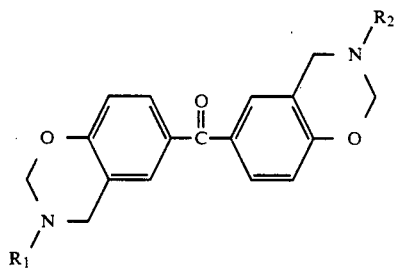

hereinafter referred to as "Compound 1", and

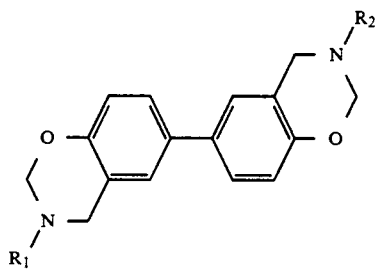

hereinafter referred to as "Compound 2", wherein $R_1$ and $R_2$ are organic radicals which may be the same or different, and pyrolyzing said compound to form a carbon-carbon composite.

The preceding and additional aspects of this invention are provided by the process of the preceding paragraph wherein said benzoxazine compound is selected from the group consisting of

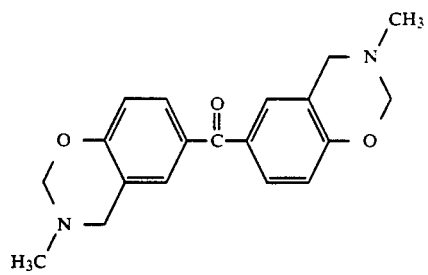

hereinafter referred to as "Compound 4",

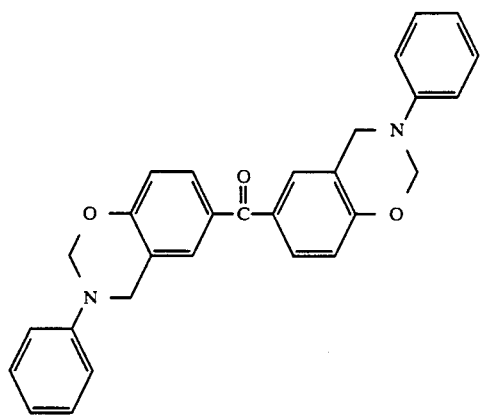

hereinafter referred to as "Compound 5",

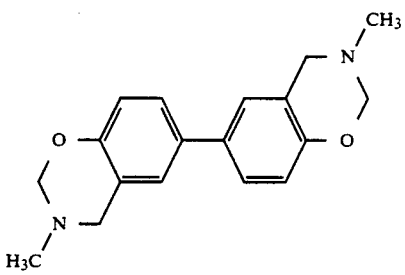

hereinafter referred to as "Compound 6", and

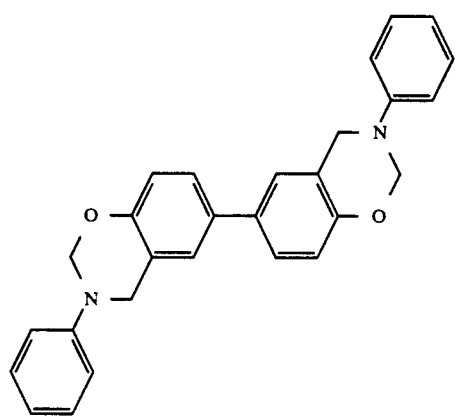

hereinafter referred to as "Compound 7".

The preceding and yet additional aspects of the invention are provided by a compound useful for forming carbon-carbon composites selected from the group consisting of Compound 4, Compound 5, Compound 6, and Compound 7.

The preceding and still other aspects of the invention are provided by an article fabricated from a carbon-carbon composite formed by a method comprising impregnating carbon fibers with a multi-functional benzoxazine compound and pyrolyzing said compound to form a carbon-carbon composite.

DETAILED DESCRIPTION OF THE INVENTION

Benzoxazine compounds are heterocyclic compounds synthesized as Mannich reaction products from their corresponding phenols, primary amines and formaldehyde. Compounds with bi-functional benzoxazine groups form characteristic phenolic material structures through a ring-opening reaction mechanism to provide cross-linked network structures. While poly-functional benzoxazines have been previously used in coatings and for encapsulation, it has now been discovered that certain poly-functional benzoxazine compounds provide significant advantages in the preparation of carbon-carbon composites. The benzoxazine compounds of the invention are characterized in having unusually low viscosities in comparison to compounds normally employed as impregnating materials for carbon-carbon composites. In addition, and most importantly, particular benzoxazine compounds exhibit remarkable char yields upon being pyrolyzed, significantly reducing the number of carbonization cycles required to densify the carbon fiber structures from which they are prepared. In the latter regard, it has surprisingly been found that there are significant differences in the amount of char produced by different benzoxazine compounds, some such compounds unexpectedly being exceptionally suitable for forming carbon-carbon composites, while others produce significantly less char.

Multi-functional benzoxazines of the invention are prepared by the condensation of a multi-functional phenol, formaldehyde, and a primary amine. Bi-functional benzoxazines have been found to be particularly useful for purposes of the invention, although tri-functional and benzoxazine compounds possessing even higher functionality may also be employed for the purpose. A typical reaction employed in forming the benzoxazine compounds of the invention is that involving, for example, the formation of a benzoxazine utilizing bisphenol-A, methylamine, and formaldehyde in the following reaction:

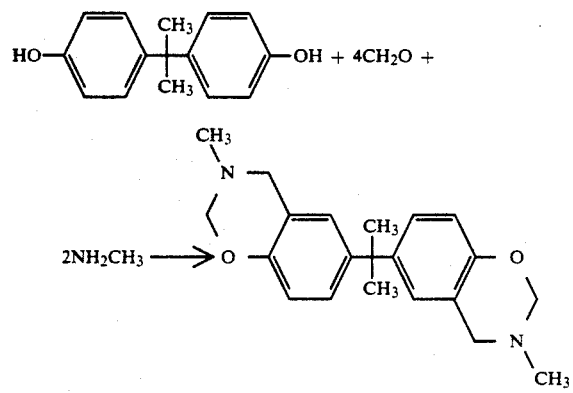

Benzoxazine rings are capable of undergoing ring-opening polymerizations in a variety of ways, including thermal initiation in the absence of a catalyst to form phenolic resins in accordance with the following reaction:

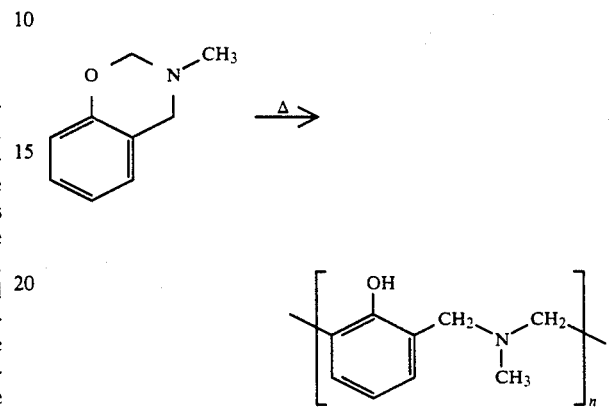

Among the benzoxazine compounds suitable for the purposes of the invention, certain benzoxazines are particularly preferred as previously stated. Such compounds include the following:

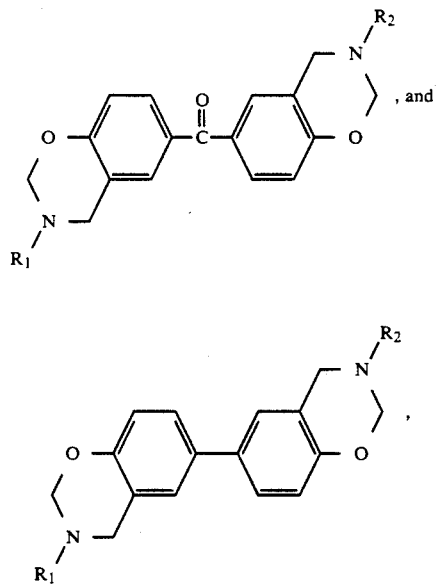

wherein $R_1$ and $R_2$ are organic radicals and may be the same or different. Preferred radicals include alkyl groups, phenyl groups, saturated cyclic groups, siloxane groups and others.

An additional compound useful as a carbon-forming precursor compound, however, is a benzoxazine having the formula:

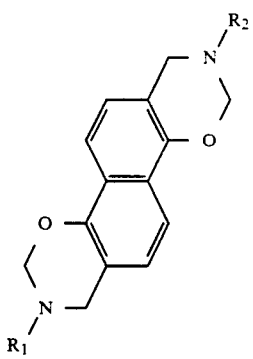

where $R_1$ and $R_2$ have the significance previously indicated, hereinafter referred to as "Compound 3".

With respect to preferred compounds, it has been found that when the multi-functional connected benzoxazines of the type contemplated by the invention possess a conjugated double bond structure at their point of connection, the benzoxazine structures are likely to be characterized by having a strong linkage with each other, providing the precursor with superior charring ability.

In preparing the multi-functional benzoxazine compounds of the invention, a typical procedure involves mixing an aqueous solution of formaldehyde in a solvent, for example, dioxane; with a primary amine such as, for instance, a solution of methylamine; and thereafter adding a multi-functional phenol, for example, bisphenol-A, also dissolved in a solvent. After heating the solution until the reaction is substantially complete, the solvent is removed by evaporation and the reaction product redissolved in a suitable solvent, ethyl ether being typical. The solvent-polymer solution is then washed to remove any unreacted components, after which the solvent is evaporated to provide the desired product, being a mixture of precursor compounds including the monomer, together with its dimers and higher oligomers.

It has been found that the molecular weight distribution of precursor compounds within the mixture depends to a large extent upon the nature of the solvent used for the synthesis. In dioxane, for instance, the majority of the composition is di-functionally terminated benzoxazine monomer, with about 30-40% by weight of the composition consisting of dimers and higher oligomers formed from the monomer. Generally speaking, it is believed that as the solvent polarity increases, the reaction between the benzoxazine structures and the free phenol structures present becomes more facilitated, resulting in less free monomer and more oligomers existing at the end of the reaction.

The benzoxazine materials of the invention have been found to be excellent impregnating materials for carbon-carbon composites due to their low melt viscosity, probably the result of the lack of phenolic hydroxyl groups which would otherwise produce hydrogen bonding in the precursor compounds. Typically, the viscosity of the precursor compounds of the invention will range from only about 100 to 300 centipoise at 120° C.

Furthermore, and as previously indicated, the benzoxazine compounds of the invention undergo ring opening polymerization at elevated temperatures, leading to cross-linking reactions that prevent the loss of the precursors as the temperature of the impregnated composite is raised in the carbonization process. Cross-linking of the benzoxazine monomer, for example, usually takes place from about 150° C. to about 250° C., after which the precursors are immobilized within the composite structure. Because of the above-described characteristics, the benzoxazine precursor compounds provide excellent wetting of the composite structure during the impregnation process and yet become fixed within the structure during the heating phase of the carbonization process, assuring that the precursors are retained therein to provide the carbon required for densification.

With respect to the carbonization process, as previously indicated, a wide variety of carbonizing precursor materials have in the past been used to prepare carbon-carbon composites. Table 1, below, lists various precursor materials, including some of the ones previously used in the industry.

TABLE 1

| Material | % Char @ 850° C. |
|---|---|
| Coal Tar Pitch[1] | 25 |
| Phenolic Resin A[1] | 39 |
| Phenolic Resin B[1] | 51 |
| Coal Tar Pitch[1][2] | 72 |
| Polyphenylene (HA 43)[1][3] | 84 |
| Compound 4 | 65 |
| Compound 5 | 65 |
| Compound 6 | 62 |
| Compound 7 | 62 |
| Compound 8[4] | 33 |
| Compound 9[5] | 28 |

[1]Fitzer, Erich. The Future of Carbon-Carbon Composites. 1986.
[2]Carbonization conducted at a pressure of 100 bars
[3]Marketed by Kennedy & Klein Inc.
[4]Shown in Example 1
[5]Shown in Example 2

The list includes various benzoxazine compounds, some being the preferred compounds of the invention. It will be observed that of the materials listed in the table, only two, coal tar pitch and polyphenylene (HA 43) show greater char than the preferred compounds of the invention, i.e., Compounds 4, 5 6 and 7. However, with respect to such two, the value shown for coal tar pitch was obtained only by carrying out the carbonization procedure at 100 bars. Furthermore, while the char value in the case of the polyphenylene material is exceptional, that material suffers from the fact that it is not only expensive but exhibits a high viscosity, making it difficult to employ in a composite impregnation process.

Of particular interest is the fact that although the benzoxazine compounds, that is, Compounds 4 through 9, are structurally relatively closely related, there is an unexpectedly large difference in their charring properties. In this regard, the preferred benzoxazines of the invention shown in the table, Compounds 4 through 7, have been found to provide approximately twice the amount of charring as the other benzoxazine Compounds 8 and 9. This unexpected result explains why among the benzoxazine compounds of the invention, such compounds are in a preferred category.

The carbon materials used in preparing the carbon-carbon composites employing the benzoxazine compounds of the invention are typically filamentary in character, for example, structures formed by carbon fibers, particularly sheets of carbon filaments, disposed in any of a variety of configurations such as unidirectional, two-directional, three-directional or multi-directional arrangements. Within the composite, the fibers themselves, which control the strength and thickness of the material, comprise the backbone of the composite. The filamentary structure is impregnated with the precursor material by any of a number of techniques including dipping, spraying, painting and the like. Where the precursor material is solid or viscous at ambient temperatures, it will advantageously be heated to comprise a low viscosity liquid prior to the impregnation.

The impregnated structure is thereafter subjected to carbonization in a pyrolysis step, commonly carried out from 800° to 900° C., or higher, for substantial periods of time, for instance, up to three days or more. In carrying out pyrolysis of the impregnated composite structures, the temperature is normally raised relatively gradually until the desired carbonization temperature has been reached. With respect to char formation, there appears to be little difference between benzoxazine compounds that have been cured prior to pyrolysis, and those that are cured as the temperature rises during the pyrolysis process.

Heating is carried out under an inert atmosphere, for example, under nitrogen, and the composite cooled to room temperature following carbonization. After cooling, the composite is again impregnated with the carbon-forming precursor and the carbonization process repeated. The densification cycle described is repeated as often as necessary to achieve the composite density required.

With respect to the density of the carbon-carbon composites, the composites typically display a bulk density in the order of 1.2-1.3 gms per cc, after the first impregnation/carbonization cycle, and eventually approach about 1.7 to about 1.8 following repeated impregnation carbonization cycles. Consequently, repeated impregnation and carbonization of the carbon structures allows the obtainment of a composite having a density appreciably higher than that of the original carbon structure.

The following examples, while not to be construed as limiting in nature, are illustrative of the invention.

EXAMPLE 1

In this example, a benzoxazine compound is prepared having the following structure:

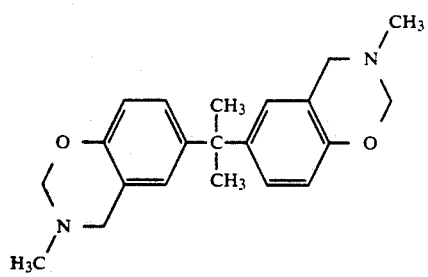

In the preparation approximately 18.6 gms of a 30% methylamine solution in methanol (0.2 moles), diluted by 20 ml of dioxane, is slowly added to a mixture of 32.4 gms (0.4 moles) of a 37% aqueous solution of formaldehyde in 80 ml of dioxane, the mixture being contained in a 500 ml, 3-neck flask equipped with a thermometer, condenser and a dropping funnel, and cooled by immersion in an ice bath. The temperature is maintained below 10° C. and the mixture stirred magnetically for ten minutes before a solution of 22.8 gms (0.1 moles) of bisphenol-A in 100 ml of dioxane is added. The temperature is raised and the mixture refluxed for six hours, resulting in the formation of a clear solution. The solvent is then evaporated in a rotovap, and the viscous liquid dissolved in 200 ml of ethyl ether. The ether solution is thereafter washed several times with water to eliminate any unreacted formaldehyde and methylamine and then dried over sodium sulfate. Subsequent evaporation of the ether results in a product which is a relatively viscous fluid at room temperature. The composition and structure of the product is analyzed by proton nuclear magnetic resonance (NMR) spectroscopy in $CD_3Cl$, as well as gel permeation chromatography (GPC) and Fourier Transform Infrared spectroscopy (FTIR) to confirm presence of the structure indicated.

EXAMPLE 2

In a subsequent experiment using a procedure similar to that of Example 1, 18.6 gms (0.2 moles) of aniline in 20 ml of dioxane is added to 32.4 gms (0.4 moles) of a 37% aqueous formaldehyde solution in 80 ml of dioxane while maintianing the mixture at a temperature below 10° C. Thereafter, 22.8 gms (0.1 moles) of bisphenol-A in 100 ml of dioxane is added to the mixture, and the mixture is refluxed for about six hours. The dioxane solvent is then evaporated in a rotovap, and the product dissolved in ethyl ether. The ethyl ether is subsequently washed with water and dried over sodium sulfate to yield a relatively viscous precursor having the following structure:

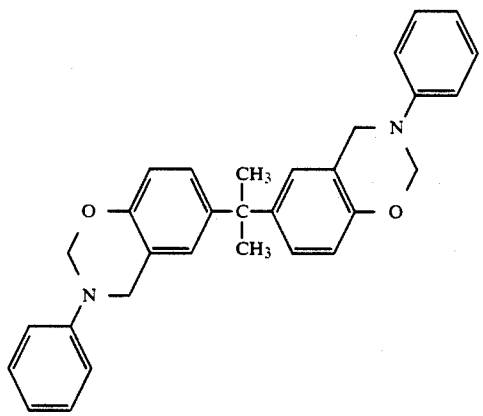

EXAMPLE 3

In a further experiment a precursor having the following structure is formed:

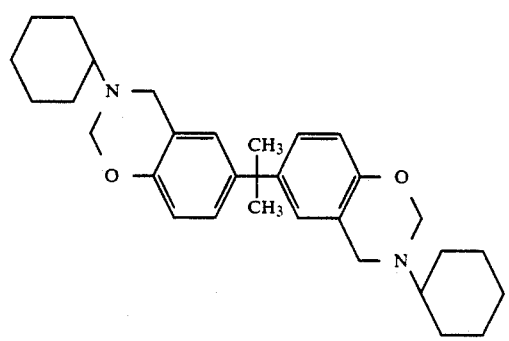

The procedure is similar to that described in connection with Example 1. In the experiment, 9.8 gms (0.1 moles) of cyclohexanamine is slowly added to 16.2 gms (0.2 moles) of a 37% aqueous formaldehyde solution in 50 ml of dioxane. A large amount of white precipitate is observed which is subsequently solubilized by the addition of a further 40 ml of dioxane. 11.4 gms (0.05 moles) of bisphenol-A in 40 ml of dioxane is thereafter added, and the mixture refluxed for approximately six hours. The solvent is then evaporated with a rotovap and the relatively viscous fluid remaining is dissolved in about 200 ml of ethyl ether. The ether solution is thereafter washed several times with water to remove unreacted methylamine and formaldehyde and dried over sodium sulfate. Evaporation of the ether produces the product in the form of a relatively viscous fluid at room temperature.

EXAMPLE 4

In this experiment, Compound 4 is prepared in a procedure similar to that of Example 1, involving the addition of 4.6 gms of a 30% methylamine solution in methanol (0.05 moles) to 8.1 gms of a 37% aqueous solution of formaldehyde (0.1 moles) in 50 ml of dioxane. The temperature of the mixture is maintained below 10° C. during the addition. Thereafter, 5.35 gms (0.025 moles) of 4.4'-dihydroxybenzophenone in 50 ml of dioxane is added to the mixture, which is then refluxed for six hours. The solvent is subsequently evaporated in a rotovap to obtain 8.8 gms of a relatively viscous fluid which solidifies upon cooling.

EXAMPLE 5

In another experiment, Compound 5 is formed using the procedure of Example 4 with the exception that the methylamine is substituted by 4.65 gms (0.05 moles) of aniline. 11.0 gms of an orange viscous fluid is thereby obtained as product which solidifies upon cooling. The resulting yield is approximately 97%.

EXAMPLE 6

In an additional experiment, Compound 6 is prepared by a procedure similar to Example 1 in which, however, 49.2 gms of a 30% methylamine solution in methanol (0.1 moles) is added to 16.2 gms of a 37% aqueous formaldehyde solution (0.2 moles) in 80 ml of dioxane. The temperature of the mixture is maintained under 10° C. during the addition. Thereafter, 9.3 gms (0.05 moles) of 4.4'-dihydroxybiphenyl in 50 ml of dioxane is added to the mixture, which is allowed to reflux for six hours. The solvent is then evaporated in a rotovap to obtain 14.5 gms of a relatively viscous fluid which solidifies upon cooling. The yield is calculated to be 96%.

EXAMPLE 7

Compound 7 is prepared in an experiment conducted in similar fashion to that of Example 6 except that methylamine is substituted by 9.3 gms (0.1 moles) of aniline. The resulting orange, relatively viscous fluid, 20.1 gms, solidifies upon cooling to give a yield of 95%.

EXAMPLE 8

Compound 3, in which R is a phenyl group, is prepared in a procedure conducted similarly to that described in connection with Example 1 in which 14.0 gms (0.15 moles) of aniline in 20 ml of dioxane is slowly added to 24.3 gms (0.3 moles) of an aqueous solution of formaldehyde in 100 ml of dioxane. Thereafter, 12.0 gms (0.075 moles) of 1.5-dihydroxynaphthalene in 60 ml of dioxane is added and the solution allowed to remain overnight at a temperature sufficient to cause the mixture to reflux. The light-brownish precipitate produced is filtered out and washed with dioxane and methanol, respectively. The precipitate is totally soluble in both tetrahydrofuran (THF) and chloroform, and is determined to consist essentially of the benzoxazine product intended.

EXAMPLE 9

In a further experiment, a compound having the structure

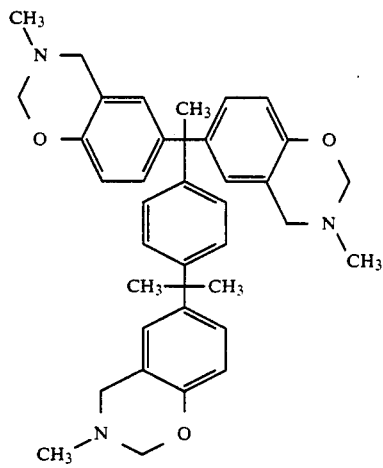

is prepared by adding 7.0 gms (0.075 moles) of a 30% methylamine solution in methanol to 12.2 gms (0.15 moles) of a 37% aqueous solution of formaldehyde in 60 ml of dioxane, the mixture being maintained below 10° C. during the addition. Subsequently, 10.6 gms (0.025 moles) of the tri-functional trisphenol-PA, marketed by Kennedy & Klein Inc., in 50 ml of dioxane is added. The solution is refluxed overnight and the solvent removed by processing in a rotovap. The residue is then dissolved in ethyl ether and washed with water before being dried over sodium sulfate. Following removal of the solvent, a clear relatively viscous product is obtained.

Each of the products obtained as described in the preceding examples produces significant amounts of char, including the values shown in Table 1, upon being subjected to pyrolysis to 850° C. under flowing high purity nitrogen in a thermogravimetric analyzer adjusted to provide a rate of temperature rise of about 20° C. per minute. While the products range from solids to viscous fluids, they produce liquids with very low viscosities upon being heated to temperatures still below their curing temperatures, thus lending themselves to the impregnation of filamentary carbon structures of the type employed in fabricating carbon-carbon composites. Furthermore, the products are of a type that cure during the carbonization cycle used in the preparation of the composites, thereby allowing their retention in the structure during pyrolysis. In some instances, as more particularly described in connection with Table 1, the degree of char is exceptional, allowing those composites to be formed with a minimum number of densification cycles.

While in accordance with the patent statutes, a preferred embodiment and best mode has been presented, the scope of the invention is not limited thereto, but rather is measured by the scope of the attached claims.

What is claimed is:

1. A process for forming a carbon-carbon composite comprising impregnating carbon fibers with a multi-functional monomeric benzoxazine compound, polymerizing said compound and pyrolyzing said polymerized compound to form a carbon-carbon composite said compound including benzoxazine structures joined to each other through a bridge which has conjugated unsaturation associated therewith.

2. A process according to claim 1 in which said benzoxazine compound is bifunctional.

3. A process according to claim 1 in which said impregnation and pyrolysis are repeated a plurality of times.

4. A process for forming a carbon-carbon composite comprising impregnating carbon material with a monomeric benzoxazine compound selected from the group consisting of

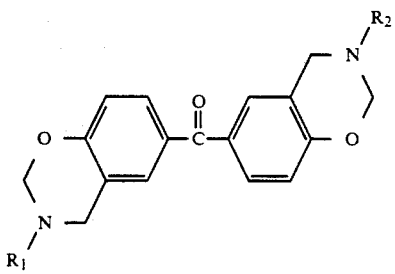

and

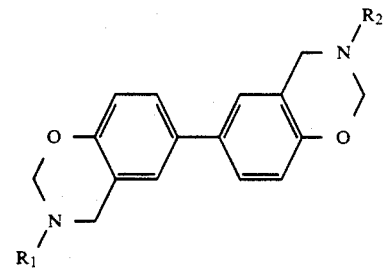

where $R_1$ and $R_2$ are radicals selected from the group consisting of an alkyl group, a phenyl group, a saturated cyclic group, and a siloxane group, which may be the same or different, polymerizing said compound and pyrolyzing said polymerized compound to form a carbon-carbon composite.

5. A process according to claim 4 wherein said benzoxazine compound is selected from the group consisting of

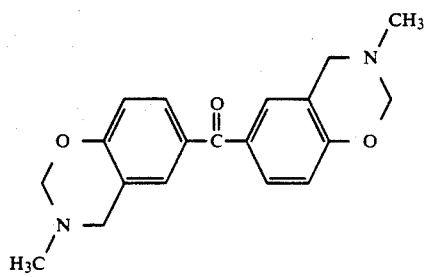

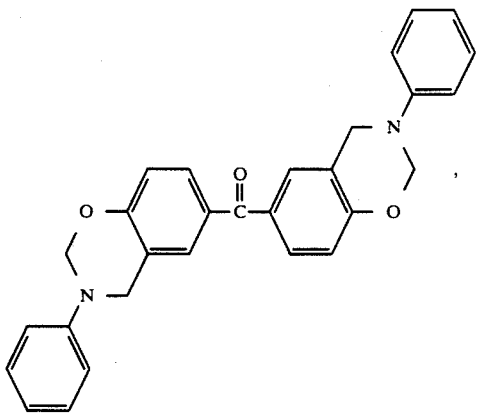

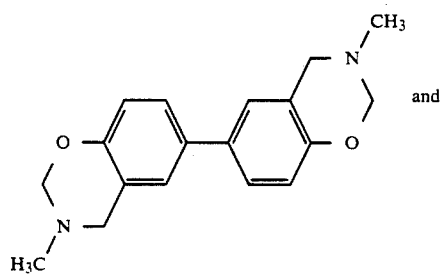

and

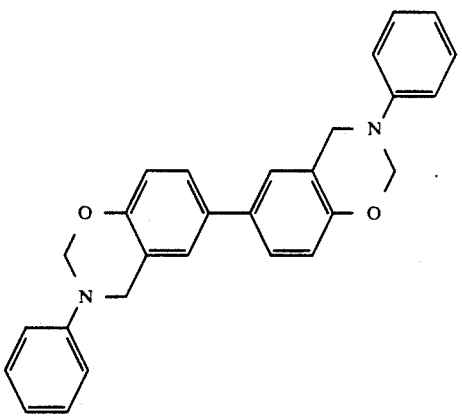

6. A process for forming a carbon-carbon composite according to claim 5 in which said carbon material is comprised of filamentary material.

7. A process according to claim 5 in which the impregnation and pyrolysis is repeated a plurality of times.

8. A process for forming a carbon-carbon composite comprising impregnating carbon material with a multi-functional monomeric benzoxazine compound, polymerizing said compound and pyrolyzing said polymerized compound to form a carbon-carbon composite, said compound being

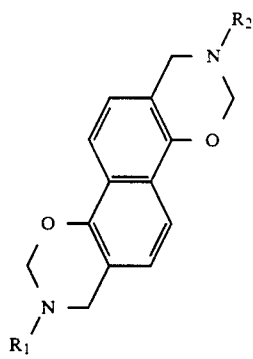

in which R₁ and R₂ are radicals.

9. A process for forming a carbon-carbon composite comprising impregnating carbon material with a multifunctional monomeric benzoxazine compound, polymerizing said compound and pyrolyzing said polymerized compound to form a carbon-carbon composite, said compound being

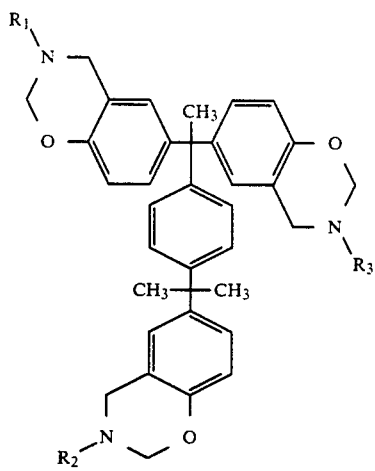

in which $R_3$ is a radical which may be the same or different from organic radicals $R_1$ and $R_2$.

10. A process according to claim 9 in which $R_1$, $R_2$ and $R_3$ are radicals selected from the group consisting of an alkyl group, a phenyl group, a saturated cyclic group, and a siloxane group.

* * * * *